United States Patent [19]

Yannas et al.

[11] 4,418,691
[45] Dec. 6, 1983

[54] METHOD OF PROMOTING THE REGENERATION OF TISSUE AT A WOUND

[75] Inventors: Ioannis V. Yannas, Newton Center; John F. Burke, Belmont; Dennis P. Orgill, Cambridge; Eugene M. Skrabut, Beverly, all of Mass.

[73] Assignee: Massachusetts Institute of Technology, Cambridge, Mass.

[21] Appl. No.: 315,234

[22] Filed: Oct. 26, 1981

[51] Int. Cl.$^3$ .............................................. A61L 15/00
[52] U.S. Cl. .......................................... 128/156; 3/1
[58] Field of Search .................... 128/155, 156, 1 R; 604/890, 891, 266; 3/1; 424/34, 35, 94, 31, 32

[56] References Cited

U.S. PATENT DOCUMENTS

| | | | |
|---|---|---|---|
| 3,826,678 | 7/1974 | Hoffmann et al. | 3/1 |
| 3,955,012 | 5/1976 | Okamura et al. | 3/1 |
| 4,326,532 | 4/1982 | Hammer | 604/266 |
| 4,352,883 | 10/1982 | Lim | 3/1 |

*Primary Examiner*—C. Fred Rosenbaum
*Assistant Examiner*—T. J. Wallen
*Attorney, Agent, or Firm*—Arthur A. Smith, Jr.; David E. Brook

[57] ABSTRACT

This invention comprises the use of centrifugal force to introduce viable cells into a fibrous lattice, as well as fibrous lattices that are seeded with cells by the use of centrifugal force. A variety of fibrous lattices may be seeded by the methods of this invention, such as a highly porous lattice comprising collagen fibers cross-linked with glycosaminoglycan. Before the centrifugation, a piece of intact tissue is harvested from a donor site. It is treated with one or more substances, such as trypsin or collagenase, to dissociate cells from the tissue. The cells are then mixed with an aqueous solution to create an aqueous suspension of cells. A piece of fibrous lattice is placed within a container, referred to herein as a "bucket," that is suitable for rotation by a centrifuge. The aqueous suspension of cells is placed within the bucket, in contact with the lattice. The centrifuge is then rotated. Centrifugal force causes the cells, which are denser than the aqueous solution, to be forced into the lattice in a relatively uniform distribution. By controlling various parameters, cells can be seeded into any desired location within a lattice.

18 Claims, 1 Drawing Figure

FLOWCHART INDICATING STEPS OF CENTRIFUGAL SEEDING METHODS

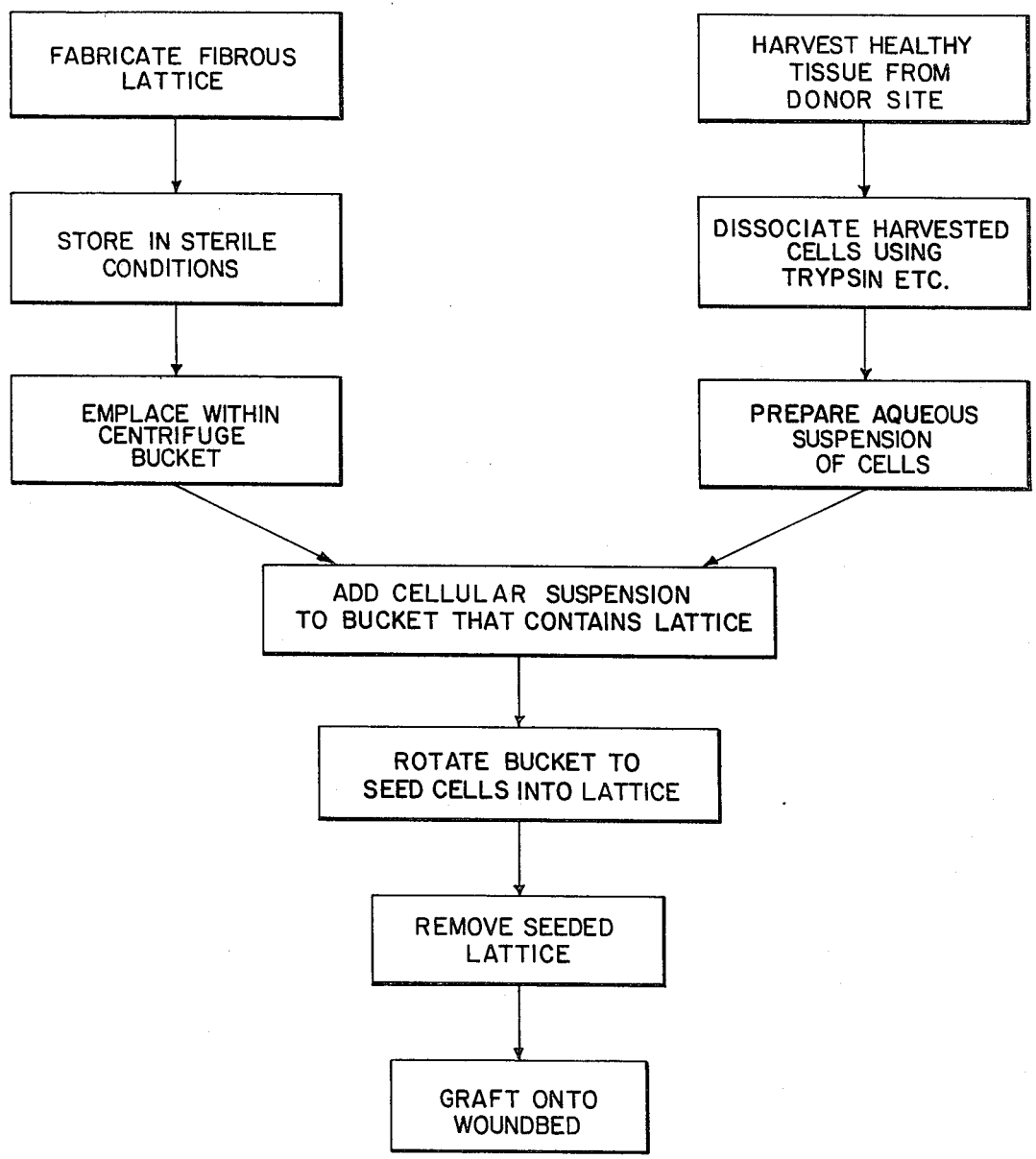

METHOD OF PROMOTING THE REGENERATION OF TISSUE AT A WOUND

GOVERNMENT SUPPORT

The invention described herein was supported in whole or in part by grants from the National Institutes of Health.

TECHNICAL FIELDS

This invention is in the fields of medicine, surgery, biology, biochemistry and polymers.

BACKGROUND ART

Damage to or loss of the skin can be a very serious injury, resulting in extreme pain, disfigurement, mutilation, and frequency death. Medical and surgical treatment of severely burned people is very time-consuming and expensive, and requires elaborate equipment and highly-trained personnel. Extensive scarring and wound contracture can lead to physiological, emotional and societal impairment.

Skin loss or injury is most commonly caused by fire or scalding, by mechanical or chemical injury, or by skin lesions. Since burns are the most common cause of skin injury, burn injury is referred to herein; however, it should be understood that, with possible minor exceptions known to those who are skilled in the art, the treatment of skin loss or damage caused by any type of injury or disease may be conducted according to the methods of this invention.

A person or animal that suffers from a burn, injury, disease, or removal of all or a portion of the skin or an organ is referred to herein as a "patient." An area of the body where tissue has been lost, damaged, diseased, or surgically removed is referred to herein as a "wound" or a "woundbed." An area of intact skin or organ from which cells are harvested, or a cell bank or tissue culture from which cells are harvested or otherwise taken, is referred to herein as a "donor site." Tissue that is regenerated by cell growth upon a wound is referred to herein as "neodermal," "neoepidermal," or "neoorgan" tissue.

Skin Structure

Normal, undamaged skin is composed of several layers [1]. The outer layer, usually called the epidermis, is composed of several types of epithelial cells. It contains nerve fibrils, but not blood vessels. The outermost layer of epidermis, usually called the *stratum corneum,* comprises squamous (i.e., relatively flat) cells that typically have low rates of reproduction; these cells are gradually sloughed off by abrasion, and are replaced by cells from the lower layers. The next lower layer is usually called the *stratum lucidum,* which may be absent in certain areas. The lowest layer of squamous cells is usually called the *stratum granulosum.* Below it are two layers of nonsquamous cells: the *stratum malpighii* (also called the *rete mucosum*) and the *stratum germinativum.*

Cells that are at or near the base of the epidermis (near the dermis) are often called basal cells. These have relatively high rates of reproduction, and may give rise to other basal cells, or to maturing epidermal cells which do not subsequently reproduce. Epidermal cells produce keratin, a protein which may be secreted or contained in cell walls. This protein is relatively hard, and imparts toughness and strength to the skin.

Below the epidermis is a layer of cells and connective tissue called the dermis. This layer comprises mesenchymal cells, which includes fibroblast cells and cells of blood and lymph vessels. Hair follicles, sebaceous glands, and sweat glands extend from the dermis to the surface of the skin; such glands and follicles are lined by epithelial cells.

Mesenchymal cells produce and secrete collagen, a fibrous protein. Such collagen forms a structural matrix that surrounds and contains the cells, which increases the strength of the tissue.

The interface between the dermis and epidermis is folded and papillary, rather than flat or level. Therefore, a burn that is relatively level may remove all of the epidermis and part of the dermis at numerous locations, while leaving clusters of intact epidermal cells interspersed in the damaged area. A burn that is somewhat deeper may remove all of the surface layers of epidermal cells (and some dermal cells as well), without destroying the epithelial cells that line hair follicles and sebaceous and sweat glands. If this occurs, the epithelial cells from the follicles and glands may proliferate and migrate over the wound, creating a shallow layer of epidermis. Such a layer is often irregular and thin, and it may impede proper healing of the wound. Either of the burns discussed above is classified as a second degree burn. A burn that destorys the epidermis and the full thickness of the dermis, including the epithelial cells that line follicles and glands, is classified as a "full thickness" or third degree burn [2].

Burn Treatment

A patient who has suffered extensive skin loss or injury is immediately threatened by infection and by excessive loss of fluids. To meet both of these needs, a severe skin wound must be closed promptly by some type of membrane. A variety of attempts have been made to meet this need. References to papyrus or animal skin date back to about 1500 B.C. Specially prepared pigskin is often used by surgeons today because of its ready commerical availability. These xenografts (i.e., membranes of non-human origin) can cover a wound for about three to five days. However, they are rejected by the patient, leaving behind an open wound. Therefore, they must usually be removed or changed after a few days, and serve essentially as a stopgap while the patient's skin slowly heals [3].

Homografts, also called allografts, can be obtained from human cadavers. However, they are in short supply and, like xenografts, are commonly rejected after a brief period. Immunosuppressive drugs may be used to delay or reduce the rejection of xenografts or homografts, thereby extending the period that they may cover a woundbed. However, the use of immunosuppressive drugs increases the vulnerability of the patient to infection [4].

Autografts are partial-thickness sections of skin which are removed ("harvested") from an undamaged area of the patient or possibly from the patient's identical twin, and transplanted onto a wounded area. Unlike xenografts or homografts, autografts are not rejected by the patient; instead, they become permanently attached to the wound and proliferate, thereby providing a new layer of epidermis and dermis which closes the wound [5].

The harvesting operation is usually performed with an instrument called a dermatome, which contains an oscillating blade and adjusting devices that control the depth and the width of the cut [6]. Since cells in the *stratum corneum* normally do not reproduce rapidly, virtually all harvesting operations remove cells from the *stratum granulosum*. Because of the papillary nature of skin, most harvesting operations also remove cells from the *stratum malpighii* and the *stratum germinativum*, as well as significant amounts of dermis.

The harvesting operation is a painful, invasive process, which causes scarring. It should therefore be kept to a minimum. In addition, a badly injured patient may suffer skin loss or damage on nearly all of his or her body. This may severely limit the amount of healthy, intact skin that is available for autografting. When this occurs, xenografts or homografts may be placed across the entire wound surface to control infection and dehydration; they are gradually replaced as autografts become available. Autografts may be harvested repeatedly from a donor site. In such an operation, an area of xenograft or homograft is removed and discarded, and replaced by an autograft. Each donor site must be allowed to heal before another autograft is removed from it; this requires a substantial delay, and prolongs the recovery of the patient.

In one important modification of the autografting process, a pattern of slits is cut into a piece of harvested skin. This allows the skin to be stretched into a mesh, thereby increasing the wound area that can be covered by that piece of skin [7]. After grafting, the autologous cells migrate and proliferate, closing up the gas caused by the slits. Eventually, with the aid of autografts, the entire wound area is covered by a layer of regenerated skin which is subject to various problems such as hypertrophic scarring, discomfort, and disabling contracture.

The Bilayer Membrane

The Applicants are co-inventors (along with certain other persons) of a synthetic multilayer membrane (herein referred to as a bilayer membrane) that is useful in treating skin loss or injury. See U.S. Pat. No. 4,060,081 (Yannas et al, 1977) and U.S. Pat. No. 4,280,954 (Yannas et al, 1981), the teachings of which are hereby incorporated by reference. Briefly, the top layer of this membrane comprises a polymer such as a silicone elastomer. This layer imparts several desired physical properties to the membrane, including tensile strength, suturability, control of moisture flux, and impermeability to bacteria and viruses. The bottom layer comprises a highly porous lattice made of collagen and glycosaminoglycan (GAG, also referred to as mucopolysaccharide). Various forms of GAG which may be suitable for use in this material include chondroitin 6-surface, chondroitin 4-sulfate, heparin, heparan sulfate, keratan sulfate, dermatan sulfate, chitin, and chitosan.

The Collagen/GAG lattice effectively serves as a supporting or "scaffolding" structure in or on which epithelial and mesenchymal cells from the burn victim can grow and proliferate. Its composition and structure are controlled so that it does not provoke a substantial immune response by the graft recipient, and it is slowly biodegraded into non-toxic substances that are utilized or eliminated by the body.

It is possible to control several parameters (primarily crosslinking density, porosity and GAG content) of the collagen/GAG lattice to control the rate at which the lattice is biodegraded by collagenase and other enzymes. Lattices that are biodegraded too quickly will disappear before sufficient healing occurs, while lattices that are biodegraded too slowly tend to impede cell migration and to cause the formation of a fibrotic layer of cells surrounding the lattice. It is believed that a lattice that is biodegraded after about thirty days is preferable for use on burn patients.

When a burn patient is admitted to a hospital, areas of skin that have been entirely destroyed or severely damaged often contain dead or damaged skin, called "eschar." The eschar usually is surgically removed to prevent it from interfering with the healing process. The entire area of damaged and dead skin is excised, so that intact epithelial cells are present at the perimeter of the wound. The bilayer membrane discussed above is carefully draped across the wound surface to avoid the entrapment of air pockets between the wound and the membrane. The membrane normally is sutured to the intact skin using conventional techniques. The grafted area is then covered with a bandage.

The collagen/GAG lattice has been observed by the Applicants to reduce wound contraction. In general, wound contraction comprises horizontal motion by existing cells in, and the periphery of, the wound. It results in substantial distortion and scarring, so its prevention or reduction is very desirable.

Within a period of several days, healthy cells from the woundbed begin to migrate into and proliferate within the collagen/GAG lattice of the membrane. Mesenchymal cells and minute blood vessels migrate in a direction that is perpendicular to the plane of the membrane. Since the skin surface is regarded herein as horizontal, the direction of mesenchymal skin growth is referred to herein as vertical. Epithelial cells migrate across the surface of the lattice in a horizontal direction (i.e., along the plane of the membrane). Since burns and other skin wounds tend to be relatively shallow, mesenchymal cells need not migrate very far in order to create a neodermis. However, epithelial cells may be required to migrate great distances to create a neoepidermis and close the wound.

Within thirty days, epithelial cells are capable of migrating and proliferating horizontally a distance of about 0.75 cm. Therefore, a wound with a horizontal minor dimension no larger than about 1.5 cm could be closed by epithelial migration within about thirty days, assuming that epithelial cells are closing the wound from all sides. However, extensive burns often exceed 1.5 cm in every direction. For example, it is not unusual for a badly burned patient to lose virtually all of the skin below the shoulders. Therefore, epithelial cells cannot reach the interior areas of a large wound by normal migration for periods exceeding hundreds of days. When used with very large wounds, a collagen/GAG lattice with a biodegradation rate of about 30 days would be entirely biodegraded long before the epithelial cells could close the wound.

Preparation of an Aqueous Suspension of Cells

There are several known techniques for dissociating a cohesive piece of skin into a suspension of living, reproducing cells in a liquid solution [8]. One common technique involves treating a piece of harvested skin with trypsin, collagenase, or other enzymes that cause cells to become detached from other cells or from solid surfaces. After a piece of skin is treated with one or more enzymes, a layer of epidermis is removed and discarded. The remaining tissue, which contains basal cells that reproduce at relatively high rates, is agitated with enough force to separate the cells without damaging them. For example, stirring at low speeds, vortexing, pipetting, and other forms of mixing can be used for this purpose. The cells are usually suspended in an aqueous solution that contains various salts that resemble the substances found in body fluids; this type of solution is often called physiological saline. It may be buffered by phosphate or other non-toxic substances, in order to maintain the pH at approximately physiological levels, and it may be supplemented by animal or human blood serum or other sources of protein or other nutrition. The density of the liquid may be controlled so that it is less than the density of the cells.

DISCLOSURE OF THE INVENTION

This invention comprises the use of centrifugal force to introduce viable cells into a fibrous lattice, as well as fibrous lattices that are seeded with cells by the use of centrifugal force. A variety of fibrous lattices may be seeded by the methods of this invention, such as a highly porous lattice comprising collagen fibers crosslinked with glycosaminoglycan. Before the centrifugation, a piece of intact tissue is harvested from a donor site. It is treated with one or more substances, such as trypsin or collagenase, to dissociate cells from the tissue. The cells are then mixed with an aqueous solution to create an aqueous suspension of cells. A piece of fibrous lattice is placed within a container, referred to herein as a "bucket," that is suitable for rotation by a centrifuge. The aqueous suspension of cells is placed within the bucket, in contact with the lattice. The centrifuge is then rotated. Centrifugal force causes the cells, which are denser than the aqueous solution, to be forced into the lattice in a relatively uniform distribution. By controlling various parameters, cells can be seeded into any desired location within a lattice. Lattices that are seeded by centrifugal methods may be used to promote the growth of cells or the generation of tissue at a wound.

BRIEF DESCRIPTION OF DRAWINGS

The drawing is a flow chart indicating a sequence of steps comprising the invention.

BEST MODE OF CARRYING OUT THE INVENTION

In one preferred embodiment of this invention, a piece of epidermis containing healthy, reproducing epithelial cells is harvested from a donor site on a burn patient. This piece of epidermis is dissociated into an aqueous suspension of cells by treating it with trypsin, collagenase, or other suitable enzymes. A piece of bilayer membrane, described in U.S. Pat. No. 4,060,081 (Yannas et al, 1977) is placed on the bottom of a "swinging"-type bucket that is suitable for rotation by a centrifuge, or within a specimen holder that is suitable for placement within such a bucket. The membrane is arranged within the bucket so that the silicone layer is pressed against a wall of the bucket or the specimen holder, and the collagen/GAG lattice is exposed to the interior of the bucket. The cellular suspension is introduced into the bucket, so that the solution and the cells within it contact the collagen/GAG lattice. The bucket is then rotated to generate centrifugal force upon the lattice and suspension. The cells in the suspension, which have greater density that the liquid, are forced toward the walls of the bucket, and thereby become embedded in the collagen/GAG lattice.

The speed and duration of rotation of the bucket may be controlled to embed the epithelial cells into a lattice at a desired depth or range of depths. For example, if the bucket is rotated at sufficiently high speed for a sufficiently long period of time, a substantial number of cells will be forced through the entire thickness of the collagen/GAG lattice and will come to rest against the silicone layer. If the container is rotated at lower speed or for a shorter period of time, a substantial number of cells may be embedded at various depths within the collagen lattice.

Centrifugation may be performed in stages. For example, a collagen/GAG lattice may be fitted into a bucket, and a cellular suspension added to the bucket. The bucket may be rotated for a predetermined period of time, and then stopped. A second volume of cellular suspension may be placed in the bucket, and the bucket may be rotated again. This two-stage centrifugation may be used to seed cells into a thick lattice with more uniformity than a single-stage centrifugation. The process may be repeated any number of times.

The seeding density of cells within a lattice may be controlled, primarily with respect to the horizontal area but also with respect to the thickness of the lattice, by controlling the concentration of cells within the suspension, i.e., the number of cells within a given volume of solution or by controlling the quantity of suspension placed within.

After a membrane that has been seeded centrifugally is grafted onto a woundbed, surviving cells will reproduce and form numerous colonies of cells. Each colony will grow radially until it meets a neighboring colony. In this way, the seeded cells grow to confluence and close the wound.

A wound may be closed more quickly if cells are seeded within the membrane in a relatively dense areal pattern, i.e., if the seeded cells are closer together in the plane of the membrane, referred to herein as horizontal. The appropriate areal density will normally depend upon numerous specific factors involving the wound and the patient's condition. In general, the closure time for a wound of a given size is inversely related to the seeding density and to the size of the harvested piece of skin.

It is possible to embed more than one type of cell into a lattice using the centrifugation technique. Under the present state of cell culturing techniques, it is believed that epithelial cells tend to reproduce more rapidly when they are in intercellular communication with fibroblast or other mesenchymal cells [9]. A delay of several days normally is necessary after grafting an unseeded bilayer membrane onto a wound, before removing the silicone layer and suturing a layer of autologous cells onto the lattice. One of the purposes of this delay is to allow mesenchymal cells and blood vessels to grow vertically into the lattice from the wound-bed. However, this delay may be avoided or reduced if mesenchymal cells are harvested from the patient and centrifuged into the lattice prior to being grafted onto the wound. In one embodiment of this invention, epithelial and mesenchymal cells may be mixed within the same liquid suspension and centrifuged simultaneously into a lattice. In an alternate embodiment of this invention, epithelial cells may be centrifuged into a collagen lattice, embedding them near the silicone layer, and mesenchymal cells may then be centrifuged into the lattice. In either embodiment, at least some of the mesenchymal cells will be below (i.e., closer to the wound surface) the epithelial cells when the membrane is grafted onto the wound, and epithelial cell reproduction may begin very quickly. In another alternate embodiment, mesenchymal and/or endothelial cells may be centrifuged into the lattice in order to reduce the delay that is required before epidermis is autografted onto the lattice.

It is possible to commence the harvesting, dissociation, and centrifuging operation as soon as a patient is admitted to a hospital. All three of these procedures can be completed within the space of a few hours. Therefore, it is possible to prepare and graft a fully-seeded membrane onto a patient while the patient is still under general anesthesia during the admittance operation, while eschar is being removed from the wound. In this way, a single operation may be sufficient to clean the wound and replace it with a cell-seeded synthetic membrane that is capable of promoting full closure of the wound. This may eliminate the need for a long and painful series of operations to place xenografts or allografts on a wound, remove them before they are rejected, and eventually replace them as autografts become available.

The centrifuging procedure also reduces or eliminates difficulties that might arise in removing the silicone layer from the collagen lattice of the bilayer membrane. Over a period of several weeks or months (which can be varied by controlling certain parameters of the collagen lattice) the collagen lattice is eventually biodegraded. It is replaced by collagen which is produced and secreted by cells growing within the lattice. This collagen is produced and secreted under wet conditions, and it does not become affixed to the silicone layer. The silicone layer, which was initially attached to a lattice of dry collagen, spontaneously peels off of the collagen lattice when epidermal cells grow between the collagen lattice and the silicone layer. This eliminates the need for surgical removal or peeling of the silicone layer.

An important advantage of centrifugal seeding is that it can be used to greatly expand the area or volume of a wound that can be closed quickly by multiplication of a limited number of cells. This provides for two distinct advantages. First, if a very limited amount of intact tissue is available on a seriously burned patient, then the centrifugation method may be used to greatly increase the area or volume of a lattice that may be seeded with the limited number of available cells. Second, if a given area or volume of a lattice needs to be seeded with cells, then the amount of intact tissue that needs to be harvested from a donor site may be greatly reduced. The optimal seeding densities for specific applications may be determined through routine experimentation by people skilled in the art.

A piece of fibrous lattice or bilayer membrane may be placed directly into a centrifugal bucket, or into a specimen holder that is fitted into a centrifugal bucket. Specimen holders may be fabricated from polycarbonate, aluminum, or other materials which can be conveniently sterilized by autoclaving or other methods. Typically, a specimen holder will contain one or more depressions or "wells" into which a piece of lattice or membrane may be fitted.

A potential problem exists regarding gaps between the edge of a lattice and the wall of a specimen holder or centrifugal bucket. When driven by centrifugal force, cells in an aqueous suspension will travel to the lowest or outermost accessible area. If a large gap exists between the edge of a lattice and the wall of a specimen holder, a large number of cells will collect in the gap rather than be properly seeded in the lattice. This potential problem can be avoided or mitigated in a variety of ways, including the following.

First, a piece of membrane or lattice may be placed into a well that is the same size. A variety of specimen holders with different size wells could be kept on hand to accommodate a variety of membrane or lattice sizes. After a membrane or lattice has been centrifugally seeded, it may be trimmed to the proper size to inlay into a woundbed. Most of the cells seeded into the unused areas may be recovered if desired, by techniques such as wringing or centrifuging. To centrifugally remove cells from a seeded bilayer membrane, the membrane could be placed in a specimen holder or centrifugal bucket with the moisture transmission control layer oriented toward the axis of rotation.

Alternately, gaps that surround a lattice could be filled with impermeable material that is as thick as, or somewhat thicker than, the lattice that is to be seeded. There are several ways to accomplish this. For example, a set of impermeable sheets of plastic, the same size as the well in a specimen holder, may be kept in stock. A piece of lattice can be trimmed by a surgeon to inlay into a woundbed. The trimmed lattice may then be placed on top of a sheet of impermeable plastic. An incision through the plastic may be made along the perimeter of the trimmed lattice, allowing a piece of plastic identical in size to be removed from the sheet of plastic and discarded. The surrounding piece of plastic and the trimmed lattice may then be placed into the specimen holder or centrifugal bucket.

A variety of centrifugation techniques may be used in conjunction with this invention. For example, a quantity or a continuous flow of cellular suspension may be administered to or removed from a lattice while the lattice is being rotated.

ALTERNATE MODES OF CARRYING OUT THE INVENTION

Cells can be seeded by the methods of this invention into a porous lattice of virtually any chemical composition. Although the collagen/GAG lattices disclosed in U.S. Pat. No. 4,060,081 (Yannas et al, 1977) and U.S. Pat. No. 4,280,954 (Yannas et al, 1981) contain a relatively small weight percentage of glycosaminoglycan (GAG) to improve the biocompatibility and physical properties of the collagen, the presence of GAG or any other substance within a collagen lattice is not necessary for the purpose of this invention.

Although the research that led to this invention involved collagen, the cell seeding methods of this invention are not limited to methods for seeding collagen. Subsequent research may reveal that other fibrous proteins or other polymeric molecules may also be suitable for prosthetic or other medical purposes. If such other molecules are formed into porous lattices that are seeded by the methods of this invention, then such seeding processes, and such seeded lattices, are within the scope of this invention.

The term "lattice" is used broadly herein to include any material which is in the form of a highly porous and permeable structure in which cells can migrate and proliferate.

"Fibrous lattices" should be construed broadly to include all lattices which include material that is fibrous at the macroscopic, microscopic, or molecular level. For example, many polymeric foams comprise long organic molecules, which may have numerous side chains or extensive crosslinking. Alternatively sintered ceramic materials comprise numerous particles which may be regarded as fibrous in shape or nature. Any such material, if formed as a lattice that is seeded with cells by the methods of this invention, is within the scope of this invention.

It is possible to seed cells into lattices of any shape or configuration. For example, it may be possible to create molded bilayer membranes in the shape of a face, a hand, or another irregular surface. Such lattices may be seeded with cells by the methods of this invention, and are within the scope of this invention.

The methods of this invention may be used in combination with other methods for seeding cells into a fibrous lattice. For example, when a burn patient is first admitted to a hospital, autologous cells may be harvested from the patient, dissociated into an aqueous suspension, and centrifugally seeded into a bilayer membrane that is grafted onto the patient during the initial operation. If an insufficient number of healthy epithelial cells is available, or if some of the centrifuged cells fail to generate colonies for any reason, then areas of the wound might not be closed by neoepidermis generated from the centrifugally seeded cells. Areas of unclosed wounds can be identified by visually monitoring the transparent silicone layer of the membrane. These areas can be reseeded by one or more other methods which are the subject of a separate patent application, U.S. application Ser. No. 315,233, the teachings of which are hereby incorporated by reference. For example, large voids in the epithelial coverage may be seeded by removing an area of the silicone layer and spraying or spreading a quantity of a suspension of cells onto the exposed collagen lattice. Small gaps in the epithelial coverage may be seeded by syringe emplacement of cellular suspension.

Autologous cells, as described previously herein, were restricted to cells taken from the patient, or from the patient's identical twin. This is a reflection of the current status of grafting techniques. Using the current techniques, non-autologous cells tend to be rejected by a wound. However, subsequent advances in cell typing and matching, cell treating to remove or inactivate surface or secreted antigens or other molecules, immunosuppressive agents, and other techniques may reduce or eliminate this problem, thereby rendering non-autologous cells suitable to reconstitute lost tissue, bone, or organ. Any such cells which are matched or treated in such a manner would be suitable for seeding into a fibrous lattice by the methods of this invention. Such cells are within the scope of this invention.

Various types of fibrous lattices may be suitable for use as prosthetic devices within most regions of the body, including skin, blood vessels, bones, connective tissue, contractile tissue, and organs. Such lattices provide a structural system in which virtually any type of cell may grow, migrate, and proliferate. They can be surgically emplaced within virtually any region of the body, and if properly seeded with the appropriate type(s) of cells, may allow for the regeneration of new tissue. For example, if a patient suffers damage to or disease of an organ, a portion of the organ may need to be removed. A fibrous lattice may be emplaced in the location created by removal of part of the organ. If a sufficient number of healthy cells from another part of that organ, or from a compatible donor, is seeded into the lattice by the methods of this invention, it may be possible to greatly promote the recovery and regeneration of the organ. Such use falls within the scope of this invention. Centrifugal force may be very useful to seed cells throughout such lattices, which may be several centimeters thick in all directions.

It is possible to culture cells in vitro after they have been harvested, before they are seeded into a fibrous lattice. This would allow for several distinct advantages. For example, it can be used to increase the number of cells that are available for seeding, thereby reducing the amount of tissue that must be harvested to cover a wound. In addition, this allows for the use of cell "banks." For example, people who work in high-risk occupations could donate cells that can be cultured in vitro and available for seeding into a fibrous lattice if an accident or injury occurs. The seeding of preserved or cultured cells into fibrous lattices by the methods disclosed herein are within the scope of this invention. Cell banks and tissue cultures from which cells of a desired variety are taken for seeding are within the term "donor sites" for the purposes of this invention.

A variety of techniques are known for contacting cells with various substances that increase the reproductive rate of certain types of cells. For example, it is known that epidermal growth factor [10], fibronectin [11], cyclic nucleotides [12], choleratoxin [13], platelet derived growth factor [14], tissue angiogenesis factor [15], and various other substances [16] are capable of increasing the rate of proliferation and/or surface adherence of one or more types of cells. Prior to seeding cells into a fibrous lattice by the methods of this invention, it is possible to contact such cells with any substance that is known or hereafter discovered to increase the rate of reproduction of such cells. Such pre-seeding treatment may be used to increase the number of cells that are available for seeding, or to induce the cells to reproduce more rapidly after they have been seeded. Such pre-seeding treatment or neodermal surface treatment is within the scope of this invention.

Characteristics of Seeded Collagen Lattices

The invention described herein comprises a method of centrifugally seeding cells into or onto fibrous lattices. It also comprises a composition of matter which is a fibrous lattice that is seeded with cells by the method of this invention. In order to further define that composition of matter, the following information is provided regarding the collagen/GAG lattice that is further described in U.S. Pat. No. 4,060,081 (Yannas et al, 1977) and U.S. Pat. No. 4,280,954 (Yannas et al, 1981), the teachings of which have previously been incorporated by reference.

The physiological response of a wound to a grafted collagen lattice depends upon a combination of characteristics of the lattice, rather than upon any single characteristic acting as an isolated factor. Therefore, it is preferable not to specify an optimal numerical value of any single characteristic. Instead, a range of values can be specified for most characteristics, which assumes that all other characteristics are simultaneously within suitable ranges. It must also be noted that the correlations mentioned between parameters and characteristics are not exhaustive; instead, only the most direct correlations are mentioned.

1. Controllable Biodegradation.

A collagen lattice, when in biochemical communication with a wound surface, eventually is biodegraded by collagenase and other natural enzymes into non-toxic substances that are digested, utilized, or eliminated by normal bodily processes. The lattice must retain its structural integrity until an adequate number of cells have reproduced within the lattice to regenerate the lost or removed tissue. If the lattice is biodegraded more quickly than this, it will be liquified and rendered useless before the wound has healed. On the other hand, research by the Applicants indicates that if the lattice is biodegraded too slowly, it tends to promote the formation of a dense fibrotic sac surrounding the lattice. This sac impedes the healing of the wound and tends to exacerbate scarring.

Research with the bilayer membrane indicates that the ideal biodegradation rate should be roughly equal to approximately 25 to 30 days. This does not mean that the entire lattice should be biodegraded within 30 days. Instead, it indicates that a significant amount of biodegradation should commence within about 30 days, although remnants of the lattice may persist for several months or more. Routine experimentation by persons skilled in the art might indicate that this biodegradation rate should be modified somewhat for lattices that are seeded with cells, or for lattices that are used for purposes other than synthetic skin.

The biodegradation rate of a collagen lattice may be decreased (i.e., the lattice will endure for a longer period of time after grafting onto a wound) by increasing the collagen crosslinking density, by increasing the content of GAG that is crosslinked with collagen, or by decreasing the porosity of the lattice.

The silicone layer of the bilayer membrane is not biodegradable. However, this is satisfactory and even preferable, since this layer is spontaneously ejected (without requiring surgical invasion or removal) after neoepidermal tissue has been regenerated below it.

2. Non-antigenic and non-inflammatory.

Xenografts, allografts, and transplanted organs normally contain cells that are recognized as foreign by the immune system of the patient. In a typical immune response, antibodies and certain types of cells such as lymphocytes identify and take part in the attack on foreign cells unless immunosuppressive drugs are used to suppress the formation of antibodies or defensive cells. However, the use of such drugs renders the patient more vulnerable to infection. The use of such drugs can be rendered unnecessary if the grafted substance does not have antigenic or inflammatory properties.

The collagen/GAG lattice that has been co-invented by the Applicants may be manufactured so that it does not possess antigenic or inflammatory properties, by adjusting the chemical content and crosslinked structural arrangement of the collagen and GAG molecules. If properly prepared, it is readily accepted by wound surfaces without provoking rejection by the patient.

3. Affinity for a Wound Surface.

A collagen lattice must possess sufficient affinity for a wound surface to efficiently wet the surface and maintain contact with it. This affinity is usually expressed as surface tension or surface energy of an interface, measured in terms of force per area. The surface energy of an interface between a wound and a collagen lattice should be lower than the surface energy of an interface between the wound and the atmosphere. This criterion is satisfied by the collagen/GAG lattice coinvented by the Applicants.

4. Tensile Strength.

A synthetic membrane or prosthetic device should be sufficiently tough and strong to withstand suturing without tearing, and to prevent or limit tearing if subjected to accidental stresses caused by bandaging or medical operations or by patient movement. The two most important indices of strength of a lattice are tensile strength (which measures how much force is required to pull apart a specimen with a known cross-sectional area) and fracture energy (which measures how much work is required to create a tear of a given size). The collagen/GAG membrane has a tensile strength range of approximately 50 to 1,000 psi, and a fracture energy that ranges from approximately $1 \times 10^5$ to about $5 \times 10^6$ ergs/cm$^3$. The strength of the lattice may be increased by increasing the crosslinking density or by decreasing the porosity of the lattice.

5. Morphology.

In general, "morphology" relates to the size and spatial arrangement of the fibers within a lattice. As such, it may be regarded as the converse of "porosity," which relates to the size, shape, and spatial arrangement of the open spaces between the fibers within a lattice.

A synthetic collagen lattice that serves as a prosthetic device should resemble the collagen matrix that exists naturally within the type of tissue that is to be regenerated. This spatial arrangement will promote the growth of cells in orderly patterns that resemble undamaged tissue, thereby reducing scarring and promoting proper functioning of the regenerated tissue.

Significant morphological characteristics of a porous collagen lattice include:

a. Volume fraction of the fibers, which is equal to the volume occupied by the fibers, divided by the total volume of the lattice. This fraction is the converse of porosity, which is discussed below.

b. Mean aspect ratio, which is the ratio of the average length of the fibers to the average width. A lattice composed of long and thin fibers would have a high mean aspect ratio.

c. Mean orientation of fiber axes, which indicates whether the fibers are randomly oriented in all directions, or whether substantial numbers of fibers are oriented in roughly parallel directions along one or more axes within the lattice.

d. Mean distance between fiber axes, which indicates how far apart adjacent fibers are. This characteristic is directly related to pore size.

It is believed that the porous collagen/GAG lattice that has been co-invented by the Applicants has morphological characteristics that resemble the collagen matrixes that exist normally in mammalian skin, corneas, and tendons. Therefore, the aforementioned lattice is very suitable as a prosthetic device to promote the regeneration of lost or damaged skin, corneas and tendons. Research may indicate that other types of tissue also have similar morphological characteristics, and thus may be well-suited to regeneration by the collagen/GAG lattice described above. In addition, research may indicate methods of altering the morphological characteristics of collagen lattices to resemble the collagen matrixes that exist in other types of tissue. Such lattices, if seeded with cells by the methods of this invention, are within the scope of this invention.

6. Porosity.

Four interrelated aspects of porosity affect the rate of cell migration and reproduction within a collagen lattice:

a. Porosity, also called pore fraction, which is a fraction that is equal to the volume of the lattice. This fraction may be multiplied by 100 to convert it to a percentage. High porosity is desirable, because it provides more space in which cells can grow and multiple. Porosity may be modified to control the rate of biodegradation and the flexural rigidity of a collagen lattice.

Research involving the bilayer membrane indicates that porosity of at least about ninety percent is desirable to encourage cell migration and reproduction within or on the surface of the lattice. Additional research by the Applicants indicates that if porosity is at least about ninety-five percent, epithelial cells tend to migrate between the collagen/GAG lattice and the top silicone layer of the membrane. This is very desirable, since it allows the silicone layer to be spontaneously ejected when neoepidermal skin is regenerated beneath it.

b. Pore shape and distribution, which relates to the shape of the pores and the orientation of the fibers.

c. Pore size, which indicates the diameter of the average or mean pore. The pores within a collagen lattice must be large enough for cells to grow in and migrate through. Research by the Applicants indicates that average pore sizes of approximately 50 um tend to encourage satisfactory cell migration and reproduction. Routine experimentation by those skilled in the art may indicate that average size, and possibly the distribution of pore size about the average, should be varied to enhance cell migration and reproduction for various uses of collagen lattices.

d. Connectivity, also called permeability, whether the pores are isolated or interconnected. A closed-cell foam does not allow fluid or other material to move through it; each bubble is trapped. This type of lattice would be unsuitable for cell migration. By contrast, a permeable lattice contain spores that are interconnected; this allows the movement of fluids or cells between pores. The fibrous nature of collagen, and the freeze-drying procedures that is used to create the lattices that are used in this invention, ensure that the lattices are sufficiently permeable to permit cell migration.

7. Reduction of Wound Contraction.

Wound contraction normally involves migration of cells in and on the periphery of a wound. For example, if a small piece of skin is lost or removed from an animal or human, the surrounding skin will tend to move across the fascia to close the wound. This results in distortion and scarring of the wounded area, and it is very detrimental to accurate return to normal function. Research by the Applicants indicates that proper creation and emplacement of the bilayer membrane tends to delay and reduce wound contraction, which reduces scarring and contracture deformity and promotes the regeneration and proper functioning of neoepidermal skin.

8. Flexural Rigidity.

When placed in contact with a wound surface, a collagen lattice should be sufficiently flexible to prevent pockets of air from being trapped between the woundbed and the lattice. Such pockets of entrapped air, often called dead space, become filled with fluid and often develop into sites of bacterial proliferation and infection, and therefore should be avoided. Efficient wetting requires the use of a lattice with relatively low rigidity.

Flexural rigidity is a function of the shape of the lattice and the modulus of elasticity of the material. The rigidity of a membrane used as artificial skin may be reduced by reducing the thickness of the membrane; however, an organ or bone prosthesis may be constrained to a specific shape. The modulus of elasticity (often called Young's modulus) must be sufficiently low to reduce the flexural rigidity of a collagen lattice to acceptable levels, but sufficiently high to withstand moderate compressive forces without buckling. Materials with a Young's modulus between about 1 and about 100 psi (depending on the thickness and shape of the lattice) are preferred. The Young's modulus of a collagen lattice may be increased by decreasing the porosity or increasing the crosslinking density.

9. Moisture Flux.

Moisture flux relates to the amount of water or other liquid that will permeate through a given area of a membrane during a given period of time, expressed by $gm/cm^2/hr$ or similar terms. If the moisture flux of a membrane used as synthetic skin is too high, too much fluid will leave the wound, and the woundbed and the membrane will dehydrate, causing shrinkage and curling of the membrane. On the other hand, if the moisture flux of the membrane is too low, fluid will accumulate beneath the membrane, disrupting the desired physiological processes. Such fluid accumulation is usually called exudate or edema. To avoid either extreme, the moisture flux of a membrane used as synthetic skin should approximate the moisture flux of normal skin.

The moisture flux of the collagen/GAG membrane may be easily controlled by modifying the thickness of the silicone layer. It has been found that a silicone layer of approximately 0.1 to 1.0 mm provides a moisture flux that is in the appropriate range.

EXAMPLES

Example 1: Preparation of Bilayer Membranes

Collagen from bovine hide, prepared by the methods described by M. Komanowsky et al, *J. Amer. Leather Chemists Assn.* 69: #9, p. 410–422 (1974), was donated by the Eastern Regional Research Center, U.S. Department of Agriculture, Philadelphia, PA. It was ground in a Wiley mill (A. H. Thomas Company, Philadelphia, PA) using a 20-mesh screen, cooled with liquid nitrogen. To prepare each membrane, 0.55 g (hydrated weight) of milled collagen was added to 200 ml of 0.05 M aqueous acetic acid. This solution was stirred for 60 minutes in an ice-jacketed blender (Eberbach Corp., Ann Arbor, MI) on a 2-speed power unit (Waring Company, Hartford, CT) set on high speed with the line voltage reduced to 60 volts.

0.044 g of chondroitin 6-sulfate (hydrated weight) obtained from shark cartilage (sodium salt form, type C, Sigma Chemical, St. Louis, MO) was dissolved in 40 ml of 0.05 M acetic acid. Over a period of five minutes, the C6S solution was added to the collagen dispersion during blending. The mixture was blended for an additional 10 minutes, then centrifuged at 1500 g for one hour in a refrigerated centrifuge (Model CRU-5000, International Equipment, Needham Heights, MA) maintained at 4° C. The dispersion was removed from the centrifuge, and 140 ml of supernatant was decanted for each 240 ml of the dispersion which was centrifuged. The concentrated dispersion was then blended for 15 minutes in the Eberbach blender at high speed setting, 60 volts. The dispersion was then poured into freezing trays; 2 ml of dispersion were applied to each square inch of tray surface. The trays were placed on a precooled freezing shelf maintained at −45° C. (Model 10-MR-PC, Virtis Company, Gardner, NY). The trays were allowed to freeze and equilibrate with the shelf temperature for about one hour. The pressure in the chamber was then reduced to less than 100 mtorr, and the trays were allowed to stand for an hour. The shelf temperature was increased to 0° C. The samples were lyophilized for a then period of 24 to 48 hours.

The resulting foams were removed, wrapped in aluminum foil, and placed in a vacuum oven maintained at 105° C. and 50 mtorr for a period of about 24 hours. After removal from the oven, the foams were either stored in a dessicator, or cooled and coated with silicone adhesive.

Silicone adhesive (medical grade, Dow Silastic catalog #891, Dow Chemical Company, Midland, MI) was coated over the entire surface of the cooled foam. The silicone was coated over the foam surface that was not in contact with the freezing tray. The silicone was applied with a spatula to a thickness of approximately 0.1 to 0.5 mm. The bilayer membrane was placed silicone side down in 0.05 M acetic acid at room temperature for 24 hours to allow the silicone to cure. The membrane was then turned silicone side up and allowed to rehydrate in 0.05 M acetic acid for 24 hours at room temperature. The acetic acid was removed and replaced with 0.05 M acetic acid which contained 0.25% by volume glutaraldehyde (practical grade, catalog #8-M752, J. T. Baker Chemical Co., Phillipsburg, NJ). The glutaraldehyde cross-linking treatment lasted for 24 hours at room temperature. The glutaraldehyde solution was removed, and the material was rinsed twice in distilled, deionized water. The foam was stored in water for 24 hours at room temperature, then transferred to a storage container. It was stored in a solution of 70% isopropanol in water at 4° C. until shortly before use.

Typical characteristics of membranes prepared by these methods are indicated in Table 1.

TABLE 1

Characteristics of Bilayer Membranes Prepared as Described in Example 1

| | |
|---|---|
| Tensile strength | |
| C/GAG lattice | 2 to 5 × $10^4$ newtons/$m^2$ |
| Bilayer membrane | 7 to 10 × $10^4$ newtons/$m^2$ |
| Average pore diameter | |
| C/GAG lattice before wetting | 80 microns |
| Average porosity | |
| C/GAG lattice before wetting | 96% |
| Moisture flux | |
| Bilayer membrane | 1 to 10 mg/$cm^2$/hr |
| Bending rigidity of 1 cm wide strip | |
| C/GAG lattice | 5 to 150 × $10^{-9}$ newton-$m^2$ |
| Bilayer membrane | 10 to 500 × $10^{-9}$ newton-$m^2$ |
| Antigenicity | Very low |
| Pyrogenicity | Not detectable |
| Significant biodegradation | 25 to 30 days |
| Mean orientation of fiber axes | Random |

Example 2: Preparation of Aqueous Cellular Suspensions

Autologous cells may be harvested from a guinea pig back or from a human body using a dermatome, or from the rim of a guinea pig's ear. Harvested cells are placed in cold (4° C.) phosphate-buffered saline solution (PBS) without calcium or magnesium (catalog #17-515B, M.A. Biproducts, Walkersville, MD). Before the skin is treated with trypsin, it is transferred to warm PBS (about 30° C.). The skin is then incubated at 37° C. for 40 minutes in a solution of 2.5% trypsin in Hanks' balanced salt solution without calcium or magnesium (catalog #17-160H, N.A. Bioproducts), diluted with PBS to 0.25% trypsin. Following incubation, the epidermal layer is separated from the dermal layer and discarded. The dermal layer, which contains a relatively high number of reproductive basal cells, is transferred to tissue culture medium (Dulbecco's modified eagle medium without glutamine, catalog #12-707B, M.A. Bioproducts, supplemented with 10% fetal calf serum and L-glutamine shortly before use). This solution is then vortexed for 1.5 minutes to release basal cells from the tissue. The suspension is then filtered through sterile gauze to remove large tissue fragments.

Cell concentration is determined by using a cell counting chamber or electronic particle counter. Cell viability is determined by staining an aliquot of cells with trypan blue (Grand Island Biological Company, Grant Island, NY). The cell density is adjusted to approximately $10^6$ viable cells/ml by addition of tissue culture medium.

Example 3: Centrifugal Seeding Methods and Results

A piece of bilayer membrane (prepared as described in Example 1) approximately 1.5 by 3.15 cm in area, about 1–2 mm thickness, was placed in a specimen holder fabricated of milled polycarbonate. The holder and membrane were then placed in a swinging centrifugal bucket (International Equipment Model 353-S, Needham Heights, MA). The silicone layer of the membrane was placed against the bottom of the specimen holder, so that the collagen/GAG lattice of the membrane was exposed. About 1.3 ml of aqueous cellular suspension (prepared as described in Example 2) was placed on top of the lattice by means of a pipette; this corresponds to a seeding density of about $0.29 \times 10^6$ cells per $cm^2$. The bucket was placed in a refrigerated centrifuge (International Equipment Model CRV-5000, Needham Heights, MA) maintained at about 4° C., and rotated at about 50 g for about 15 minutes.

The seeded membrane was removed from the bucket. A strip of membrane about 1.5×0.15 cm was removed from each membrane, and subjected to biological analysis. The remainder of the seeded membrane was sutured onto a 1.5×3.0 cm wound on the back of a guinea pig. This operation was performed on about 20 guinea pigs. The operations succeeded in seeding epithelial cells into the membranes which reproduced into colonies of cells. Most of the animals were sacrificed for histological studies before the ell colonies fully closed the wounds. However, on those animals that were not sacrificed before wound closure, the cell colonies grew to confluence and created a permanent, functional layer of neoepidermis. Although the neoepidermal areas tended to lack hair follicles, sebaceous glands, or sweat glands, the neoepidermal layers tended to be smoother, less scarred, and less fibrotic than neoepidermis generated by wound contraction, unaided healing, or conventional autografting. Wound closure aided by a properly seeded collagen/GAG lattice usually occurred within about 7 to 14 days.

Example 4: Modifications of the Centrifugation Methods

Several modifications of the foregoing procedures were performed to assess the importance of several parameters. In one such modification, the concentration of viable cells in the cellular suspension was increased to about $3 \times 10^6$ cells/ml. 1.3 ml of suspension was applied to a 4.5 cm² membrane, for a seeding density of about $0.87 \times 10^6$ cells per cm². However, the rate of wound closure at the high seeding density was not substantially improved by the increase in seeding density, and the apparent condition of the regenerated epidermis after 14 days was not markedly improved.

In a second modification, the membrane and suspension were placed in the centrifuge and rotated at 500 g for 10 minutes. This figure was chosen based upon published studies indicating that cell populations in test tubes were not adversely affected by forces of such magnitude and duration. However, wound closure by membranes seeded by centrifugation at 500 g for 10 minutes was substantially inferior to wound closure by membranes seeded by centrifugation at 50 g for 15 minutes.

In order to firmly establish the fact that the cell colonies within the seeded membranes were generated by seeded cells, rather than by migration or proliferation of cells from the periphery of the wound, several guinea pigs were fitted with "island grafts" of $1 \times 2$ cm seeded membranes centered in $5 \times 6$ cm wounds. The island grafts were 2 cm from the wound periphery. Epidermal cell colonies grew in the island grafts, generating neo-epidermal tissue that was isolated from any other source of epidermal cells.

Industrial Applicability

This invention has industrial applicability in the use of fibrous proteinous lattices to promote the growth of cells and tissue.

Equivalents

Those skilled in the art will recognize, or be able to ascertain using no more than routine experimentation, numerous equivalents to the specific procedures and seeded lattices described herein. Such equivalents are considered to be within the scope of this invention, and are covered by the following claims.

REFERENCES

1. See, e.g., R. H. Sims et al, *An Introduction to the Biology of the Skin* (F. A. Davis Co., Phila., 1970); W. Montagna et al, *The Structure and Function of Skin*, 3rd edition (Academic Press, New York, 1974); H. Gray, *Anatomy, Descriptive and Surgical*, 15th edition, p. 1135 et seq. (Bounty Books, New York, 1977).
2. See, e.g., H. C. Polk, Jr. et al, editors, *Contemporary Burn Management*, p. 345 et seq. (Little, Brown & Co., Boston MA, 1971).
3. See, e.g., Polk et al, supra note 2, p. 412 et seq.
4. See, e.g, J. F. Burke et al, *Ann. Surg.* 182(3): p. 183-195 (1975).
5. See, e.g., Polk et al, supra note 2, p. 362 et seq.
6. See, e.g., Polk wet al, supra note 2, p. 385 et seq.
7. See, e,g, Polk et al, supra note 2, p. 383 et seq.
8. See, e.g., M. Prunieras, *J. Investigative Dermatology* 67; p. 58 et seq. (Williams & Wilkins, Baltimore, 1976).
9. See, e.g., R. Fleischmajer et al, *Epithelial-Mesenchymal Interaction* (Williams and Wilkins, Baltimore, 1968); R. H. Kahn et al, *In Vitro* 8: 451 (1973); R. H. Kahn et al, *J. Nat'l Cancer Inst.* 53: 1471 (1974); M. Regnier, *Acta Dermatovener* (Stockholm) 53:241 et seq. (1973); Rheinwald et al, *Cell* 6:317 (1975).
10. See, e.g., R. O. Grepp, *Recent Progress in Hormone Research* 30:533 et seq. (Academic Press, New York, 1974); R. H. Starkey et al, *Science* 189:800 (1975).
11. See, e.g., L. B. Chen et al, *Science* 197:776 (1977).
12. See, e.g., D. M. Prescott, editor, *Reproduction of Eukaryotic Cells*, p. 107 et seq. (AcademicPress, New York, 1976).
13. See e.g., A. W. Bernheimer, editor, *Mechanisms in Bacterial Toxicology* p. 53-84 (Wiley, New York, 1976); D. M. Gill, *Adv. Cyclic Nucl. Res.* 8: 85 et seq. (1977).
14. See H. N. Antoniades et al, *Proc, Natl. Acad. Sci.* 76: 1809-1813 (1979).
15. See J. Folkman et al, *J. Exp. Med.* 133:275 (1971).
16. See, e.g., H. Green, *Cell* 15: 801,805 (1978).

We claim:

1. A method of promoting the replacement of damaged or removed tissue at a wound, comprising the following steps:
    a. creating a suspension of cells in a liquid that has a lower density than said cells;
    b. emplacing a fibrous lattice in a container that is suitable for centrifugal rotation;
    c. administering said suspension of cells into said container;
    d. rotating said container at a speed and duration sufficient to embed a substantial number of cells into said lattice;
    e. removing said lattice from said container; and
    f. securing said lattice in contact with said wound.
2. A method of claim 1 wherein said cells are selected from one or more of the following types of cells: epithelial cells, mesenchymal cells, endothelial cells, bone cells, connective tissue cells, contractile tissue cells and organ cells.
3. A method of claim 1 wherein a first suspension of cells is seeded into said lattice, and a second suspension containing at least one different type of cell is seeded into said lattice.
4. A method of claim 3 wherein said first suspension contains epithelial cells and said second suspension contains mesenchymal cells.
5. A method of claim 1 wherein said cells comprise autologous cells.
6. A method of claim 1 wherein said lattice is affixed to a moisture transmission control layer.
7. A method of claim 1 wherein said lattice comprises collagen molecules.
8. A method of claim 1 wherein said lattice comprises collagen molecules that are crosslinked and covalently bonded with glycosaminoglycan.
9. A method of claim 8 wherein said glycosaminoglycan is selected from the following group: chondroitin 6-sulfate, chondroitin 4-sulfate, heparin, heparan sulfate, keratan sulfate, dermatan sulfate, chitin and chitosan.
10. A method of claim 1 wherein, prior to seeding cells into said lattice, said cells are contacted with a substance that increases the rate of reproduction of said cells.
11. A method of claim 10 wherein said substance is selected from the following group: epidermal growth factor, cyclic nucleotides, cholera toxin, platelet-derived growth factor, and tissue angiogenesis factor.

12. A method of claim 1 wherein a piece of impermeable material is placed between one or more edges of said lattice and one or more walls of said container.

13. A method of claim 1 wherein the surface energy of the interface between said lattice and a woundbed is less than the surface energy of an interface between said woundbed and the atmosphere.

14. A method of promoting the regeneration of damaged or removed tissue at a wound, comprising the following steps:
   a. creating a suspension of cells in a liquid that has a lower density than said cells;
   b. placing said suspension of cells in contact with a fibrous lattice within a container that is suitable for centrifugal rotation;
   c. rotating said container at a speed and duration sufficient to embed a substantial number of cells into said lattice;
   d. securing said lattice in contact with said wound;
   e. monitoring the growth of cells within or upon said lattice;
   f. distributing a quantity of an aqueous suspension of said cells of the desired variety into or upon the regions of said lattice where the centrifugally seeded cells are not growing adequately.

15. A method of claim 14 wherein said aqueous suspension is distributed upon said lattice by immersing a brush in said suspension, removing said brush from said suspension, and wiping said brush on said lattice.

16. A method of claim 14 wherein said aqueous suspension is distributed into or upon said lattice by administering drops of said suspension to said lattice, and allowing said suspension to permeate into said lattice.

17. A method of claim 14 wherein said aqueous suspension is distributed upon said lattice by spraying.

18. A method of claim 14 wherein said aqueous suspension is distributed upon said lattice by administering a quantity of said suspension to said exposed lattice and moving a spreading device across the surface of said lattice to spread said quantity of suspension across said lattice.

* * * * *